United States Patent [19] [11] 3,953,398
Kline [45] Apr. 27, 1976

[54] AGE RESISTANT POLYMERIC COMPOSITIONS
[75] Inventor: Richard H. Kline, Cuyahoga Falls, Ohio
[73] Assignee: The Goodyear Tire & Rubber Company, Akron, Ohio
[22] Filed: Oct. 26, 1972
[21] Appl. No.: 300,959

Related U.S. Application Data
[62] Division of Ser. No. 56,635, July 20, 1970, Pat. No. 3,714,122.

[52] U.S. Cl. ................ 260/45.85 B; 260/45.9 NC; 260/45.95 H; 260/45.9 R
[51] Int. Cl.² .......................................... C08J 3/20
[58] Field of Search ................ 260/45.85 B, 473 R

[56] References Cited
UNITED STATES PATENTS

| | | |
|---|---|---|
| 3,278,448 | 10/1966 | Lauerer et al. ............... 260/45.85 B |
| 3,280,069 | 10/1966 | Knapp et al. ................ 260/45.85 B |
| 3,285,855 | 11/1966 | Dexter et al. .................... 260/45.85 |
| 3,364,250 | 1/1968 | Dexter et al. ............... 260/45.85 B |
| 3,388,189 | 6/1968 | Mazzolini et al. .................. 260/895 |

OTHER PUBLICATIONS
Polymer Engineering and Science – July, 1966, pp. 231 to 239.

Primary Examiner—V. P. Hoke
Attorney, Agent, or Firm—F. W. Brunner; J. A. Rozmajzl

[57] ABSTRACT

Antioxidants such as 3,5-di tert.butyl-4-hydroxycinnamonitrile and ethyl 3,5-di tert.hexyl-4-hydroxycinnamate, age resistant polymers having monomeric age resistors physically combined therewith and age resistant polymeric compositions prepared by free radical polymerization techniques involving the use of said antioxidants as monomers.

5 Claims, No Drawings

AGE RESISTANT POLYMERIC COMPOSITIONS

This is a divisional application of application Ser. No. 56,635, filed July 20, 1970, and issued Jan. 30, 1973, as U.S. Pat. No. 3,714,122.

This invention relates to age resistors, age resistant polymeric compositions and processes for preparing said age resistors and age resistant compositions. More particularly, the invention relates to polymeric compositions that possess a high degree of resistance to the deleterious effects of oxidative aging over a prolonged period of time even after said compositions have been subjected to solvents which would extract at least a portion of many conventional age resistors when used to stabilize polymeric compositions.

Essentially all types of rubber, both natural and synthetic, and particularly rubbers formed from dienes, are known to be susceptible to deterioration resulting from prolonged exposure to oxidative aging. A great deal of effort has been expended by those engaged in the field of polymer technology to develop various stabilizers that will effectively inhibit the adverse effects of aging of polymeric compositions. Unfortunately, many of the commercially accepted stabilizers may be volatilized when the polymeric products are exposed to elevated temperatures and/or high vacuum over prolonged periods of time. Furthermore, they are rather quickly extracted from polymeric compositions by repeated washings with aqueous detergent solutions or organic solvents. These severe conditions are routinely encountered by garments containing rubber when they are subjected to frequent laundering or dry-cleaning.

It is therefore an object of this invention to provide age resistors and polymeric compositions that are resistant to oxidative aging. It is another object of this invention to provide a process for preparing age resistant polymeric compositions. A further object of this invention is to provide polymeric compositions that are highly resistant to oxidative aging at elevated temperatures even after repeated exposure to aqueous detergent solutions or dry-cleaning fluids. It is a still further object of this invention to provide polymers possessing antioxidants chemically bound thereto.

In accordance with the present invention age resistant polymeric compositions are prepared by polymerizing a phenolic age resistor with one or more comonomers. The phenolic age resistor which can be so used has the following structural formula:

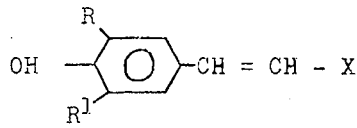

wherein R and $R^1$ are tertiary alkyl groups having 4 to 8 carbon atoms and wherein X is a radical selected from the group consisting of

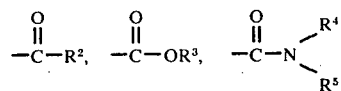

and $-CN$, wherein $R^2$, $R^3$, $R^4$ and $R^5$ are selected from the group consisting of hydrogen and alkyl groups having from 1 to 4 carbon atoms. Preferably R and $R^1$ are tert. butyl radicals although they can be tert. amyl radicals or any of the other tert. alkyl radicals having 4 to 8 carbon atoms. Preferably $R^2$ and $R^3$ are methyl or ethyl radicals. Preferably $R^4$ $R^5$ are hydrogen or methyl radicals.

Representative compounds which can be used in the present invention are:
ethyl 3,5-di tert.butyl-4-hydroxycinnamate
3,5-di tert.butyl-4-hydroxycinnamamide
3,5-di tert. butyl-4-hydroxycinnamonitrile
3,5-di tert.butyl-4-hydroxylstyryl methyl ketone
methyl 3,5-di tert.butyl-4-hydroxycinnamate
methyl 3,5-di tert.amyl-4-hydroxycinnamate
ethyl 3,5-di tert.amyl-4-hydroxycinnamate
3,5-di tert.amyl-4-hydroxycinnamonitrile
3,5-di tert.amyl-4-hydroxycinnamide
methyl 3,5-bis(1,1-dimethylbutyl)-4-hydroxycinnamate
ethyl 3,5-bis(1,1-dimethylbutyl)-4-hydroxycinnamate
3,5-bis(1,1-dimethylbutyl)-4-hydroxycinnamonitrile
3,5-bis(1,1-dimethylbutyl)-4-hydroxycinnamamide
3,5-bis(1,1-dimethylbutyl)-4-hydroxystyryl methyl ketone
ethyl 3,5-bis(1,1,2-trimethylpropyl)-4-hydroxycinnamate
3,5-bis(1,1,2-trimethylpropyl)-4-hydroxycinnamonitrile
ethyl 3,5-bis(1,1-dimethylpentyl)-4-hydroxycinnamate
3,5-bix(1,1-dimethylpentyl)-4-hydroxycinnamonitrile
ethyl 3,5-bis(1,1,3,3-tetramethylbutyl)-4-hydroxycinnamate
3,5-bis(1,1,3,3-tetramethylbutyl)-4-hydroxycinnamonitrile
n-propyl 3,5-di tert.butyl-4-hydroxycinnamate
n-butyl 3,5-di tert.butyl-4-hydroxycinnamonitrile
isopropyl 3,5-di tert.butyl-4-hydroxycinnamate
N,N-dimethyl 3,5-di tert.butyl-4-hydroxycinnamamide
N,N-diethyl 3,5-di tert.butyl-4-hydroxycinnamamide
3-tert.butyl-5-tert.amyl-4-hydroxycinnamonitrile
ethyl 3-tert.butyl-5-tert.amyl-4-hydroxycinnamate
3-tert.butyl-5-(1,1-dimethylbutyl)-4-hydroxycinnamonitrile
ethyl 3-tert.butyl-5-(1,1-dimethylbutyl)-4-hydroxycinnamate
ethyl 3-tert.butyl-5-(1,1,2-trimethylpropyl)-4-hydroxycinnamate
3-tert.amyl-5-(1,1-dimethylbutyl)-4-hydroxycinnamide
ethyl 3-tert.amyl-5-(1,1-dimethylbutyl)-4-hydroxycinnamate
methyl 3-tert.butyl-5-(1,1-dimethylpentyl)-4-hydroxycinnamate
3-tert.butyl-5-(1,1-dimethylpentyl)-4-hydroxycinnamonitrile
ethyl 3-tert.butyl-5-(1,1,3,3-tetramethylbutyl)-4-hydroxycinnamate
3-tert.butyl-5-(1,1,3,3-tetramethylbutyl)-4-hydroxycinnamonitrile
ethyl 3-(1,1-dimethylbutyl)-5-(1,1,3,3-tetramethylbutyl)-4-hydroxycinnamate
ethyl 3-tert.amyl-5-(1,1-dimethylpentyl)-4-hydroxycinnamate One of the methods by which the compounds of this invention can be prepared comprises reacting an aldehyde of the structure:

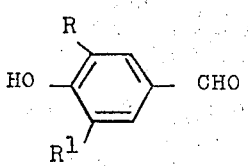

with a compound containing an active methylene group of the structure

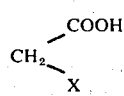

wherein X is

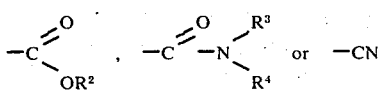

or with a methyl ketone of the structure

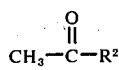

wherein R, $R^1$, $R^2$, $R^3$, and $R^4$ are as defined earlier herein, in the presence of a basic catalyst. The reaction is usually carried out by heating a solution of the reactants and of the catalyst in a suitable solvent for a period of several hours. For the reaction of an aldehyde with an active methylene compound, pyridine is the preferred solvent and secondary amines, particularly piper-idine, are the preferred catalysts. The reaction mixture is generally worked up by pouring it into a dilute hydrochloric acid solution, separating the product by filtration or extraction and purifying it as necessary. The reaction of an aldehyde with a methyl ketone is preferably carried out using an alcohol or an alcohol-water mixture as the solvent and using sodium hydroxide or a sodium alkoxide as the catalyst. This reaction mixture can also be worked up in the manner already described.

Examples of aldehydes which can be used to prepare the compounds of this invention are as follows:
3,5-di tert.butyl-4-hydroxybenzaldehyde
3,5-di tert.amyl-4-hydroxybenzaldehyde
3,5-bis(1,1-dimethylbutyl)-4-hydroxybenzaldehyde
3,5-bis(1,1,2-trimethylpropyl)-4-hydroxybenzaldehyde
3,5-bis(1,1-dimethylpentyl)-4-hydroxybenzaldehyde
3,5-bis(1,1,3,3-tetramethylbutyl)-4-hydroxybenzaldehyde
3-tert.butyl-5-tert.amyl-4-hydroxybenzaldehyde
3-tert.butyl-5--
-(1,1-dimethylbutyl)-4-hydroxybenzaldehyde
3-tert.butyl-5-(1,1,2-trimethylpropyl)-4-hydroxybenzaldehyde
3-tert.amyl-5-(1,1-dimethylbutyl)-4-hydroxybenzaldehyde
3-tert.butyl-5-(1,1-dimethylpentyl)-4-hydroxybenzaldehyde
3-tert.butyl-5-(1,1,3,3-tert.butyl-4-hydroxybenzaldehyde
3-(1,1-dimethylbutyl)-5-(1,1,3,3-tetramethylbutyl)-4-hydroxybenzaldehyde
3-tert.amyl-5-(1,1-dimethylpentyl)-4-hydroxybenzaldehyde Examples of active methylene compounds which can be used to prepare the compounds of this invention are as follows:
ethyl hydrogen malonate
cyanoacetic acid
malonic acid monoamide
methyl hydrogen malonate
N,N-dimethyl malonic acid monoamide Examples of ketones which can be used to prepare the compounds of this invention are acetone and methyl ethyl ketone.

The aforementioned monomeric age resistors may be polymerized by well known free radical polymerization techniques with one or more comonomers that are known to polymerize in free radical initiated polymerization systems. The polymerization may be carried out in emulsion, suspension, bulk or solution type systems. Some adjustments in the polymerization recipe and/or conditions may be necessary to obtain a satisfactory rate of polymer formation, depending on the amount of monomeric age resistor included and the other monomers involved. Adjustments which may be necessary in the polymerization conditions to improve polymerization rates include increasing the temperature of polymerization and/or increasing the initiator level and/or increasing the level of activator ingredients. Solvents may also be required to obtain adequate solubility of the monomers with each other as well as to solubilize other ingredients where required. Some solvents, such as methyl ethyl ketone or isopropyl alcohol, can be used to advantage with an emulsion polymerization system. These adjustements, where necessary, are to counteract the inhibitory effect of the monomeric age resistor and to insure its solubility in the system.

Examples of free radical initiators that are useful in the practice of this invention are those known as "Redox" initiators, such as appropriate combinations of chelated iron salts, sodium formaldehyde sulfoxylate and organic hydroperoxides such as cumene and paramenthane hydroperoxides. Other initiators such as azoisobutyronitrile benzoyl peroxide, hydrogen peroxide and potassium persulfate may also be used, depending on the particular polymerization system.

The special monomers used in the practice of this invention have certain chemical characteristics which preclude their use in polymerization processes other than those initiated by free radicals. By "free radical initiated systems" is meant systems wherein free radicals are generated by any of various processes such as thermal decomposition of various persulfate, perborate, peroxide, azo or azonitrile compounds; induced (catalytic or "Redox" promoted) decomposition of various persulfate, peroxide or hydroperoxide compounds and generation of free radicals by exposure of the system to high energy radiation such as radiation from a radioactive source or ultraviolet light. Such systems are very well known in the art and are widely used commercially, e.g., in the preparation of SBR, styrene/butadiene copolymers.

The most widely used system for preparation of elastomeric polymers, i.e., polymers prepared from a monomer charge made up of at least 40% diene, preferably at least 60% diene, by free radical initiation is the emulsion system. Polymers ranging all the way from liquid, low molecular weight= (mol wts. of about 1,000 to 5,000) to polymers of intermediate molecular weight (60,000 to 70,000 and higher) to oil extendable, at least 50% soluble, rubbery solid, high molecular weight (100,000 to 500,000 or more) and even highly gelled, less than 50% soluble, may be prepared by emulsion polymerization. The monomeric age resistors of the present invention can be used in such emulsion polymerization systems to produce polymers of the aforementioned type.

The principles of emulsion polymerization are discussed in references such as "Synthetic Rubber" by G. S. Whitby, Editor-in-Chief, John Wiley and Sons, 1954, particularly Chapter 8, and "Emulsion Polymerization" by F. A. Bovey et al, Vol. IX of "High Polymers," Interscience Publishers Inc. 1955. Some specialized applications of these principles are indicated in U.S. Pat. Nos. such as 3,080,334; 3,222,334; 3,223,663 3,468,833 and 3,099,650.

Some apparently have assumed that antioxidants such as sterically hindered phenols would react rapidly with free radicals of the type useful or initiating polymerization. Various techniques have been developed to obtain the desired end products by round about routes. U.S. Pat. No. 3,457,328 teaches the preparation of polymeric acid chlorides from carboxylated polymers, which in turn are reacted with various chemicals possessing chemical functions, including hindered phenols, which contribute desirable *number average molecular weights properties to the polymers to which they are attached. G. Manerke et at 99 175–185 1966)]prepared polymers using phenolic derivatives where the phenolic group was blocked by esterification or some other appropriate reaction. Then, after the polymerization step was completed, the free phenolic group was regenerated by a chemical process such as hydrolysis. The invention described herein provides a much simpler and straight forward system for building antioxidant groups into polymers.

Very effective as free radical polymerization initiators used within the practice of the present invention, when used under appropriate conditions, are compounds such as t-butyl hydroper-oxide and paramenthane hydroperoxides, and even hydrogen peroxide. These compounds perform very effectively when used in polymerization recipes containing appropriate levels of supporting ingredients. By "supporting ingredients" is meant those materials often referred to as activators in emulsion, or other systems, where required. U.S. Pat. No. 3,080,334 describes some of these materials at column 5, lines 20-26. Such materials can also be referred to as catalyst activators. The term "Redox Polymerization" is often used where the complete initiation system includes a Redox system, i.e., reducing agents and oxidizing agents in a proportion that yields polymerization initiating species. All of these initiator systems are well known in the art.

Emulsion and suspension polymerizations are normally accomplished in the range of 5° to 90° C. while the temperature range for solution or bulk polymerizations is normally 20° to 150° C. Though the activated or "Redox" initiated systems are preferred for low temperature polymerizations, they are very effective at high temperatures also, normally requiring appreciably lower quantities of the various ingredients to obtain a desirable polymerization rate.

The free radical sources used in the initiator systems are those customarily used in free radical polymerizations, for example, organic initiators such as azonitriles, azo-derivatives, peroxides, and hydroperoxides and inorganic initiators such as inorganic peroxy compounds. Radiation, e.g., of the ultra-violet and gamma type can also be used as a free radical source. Various organic initiators are described by J. Brandrup and E. H. Immergut, *Polymer Handbook* (John Wiley and Sons), 1965, pages II–3 to II–51. Peroxide initiators include the aralkyl, aliphatic, aliphatic acyl, aromatic acyl, ketone, aldehyde and perester types. Hydroperoxide compounds include aralkyl and aliphatic hydroperoxides. Inorganic peroxy compounds include persulfates, perborates, perphosphates and hydrogen peroxide.

Aralkyl peroxides are represented by dicumyl peroxide; aliphatic peroxides by di tert.butyl peroxide; aliphatic acyl peroxides by acetyl peroxide, decanoyl peroxide and lauroyl peroxide; aromatic acyl peroxides by benzoyl peroxide and 2,4-dichlorobenzoyl peroxide; ketone peroxides by methylethyl ketone peroxide and cyclohexanone peroxide; aldehyde peroxides by heptaldehyde peroxide; and perester peroxides by tert.butyl peracetate, tert.butyl perpivalate and tert.butyl perbenzoate. Aralkyl hydroperoxides are represented by cumene hydroperoxide and diisopropylbenzene hydroperoxide and aliphatic hydroperoxides by tert.butyl hydroperoxide and paramenthane hydroperoxide. Persulfate, perborate and perphosphate compunds are represented by the sodium, potassium and ammonium persulfates, perborates and perphosphates; azo-nitriles and azo-derivatives by 2,2'-azo-bis-isobutyronitrile, 2,2'-azo-bis-2-methylpropionitrile and azo-bis-diphenylmethane.

Supporting ingredients, i.e., activators capable of activating certain initiators to produce free radicals include iron compounds such as ferrous sulfate or cobalt compounds, complexed with compounds such as sodium salts of ethylene diamine tetra acetic acid or sodium or potassium pyrophosphate. Reducing agents used in Redox systems include sodium formaldehyde sulfoxylate, various sugars and hydrosulfites.

Various initiator system components are described at column 4, lines 14 to 32, in U.S. Pat. No. 3,080,334.

Examples of comonomers that are useful in the practice of this invention are polymerizable unsaturated hydrocarbons, both substituted and unsubstituted, including conjugated diene monomers, such as butadiene-1,3; 2-chlorobutadiene-1,3; isoprene; 2-ethylbutadiene-1,3; 2,3-dimethyl butadiene-1,3; piperylene; and hexadienes and copolymerizable monoolefins including vinyl and vinylidene monomers such as styrene, αmethylstyrene, divinyl benzene, vinyl chloride, vinyl acetate, vinylidene chloride, methylmethacrylate, ethylacrylate, the vinylpyridines including 2-vinyl pyridine, 5-methyl-2-vinylpyridine, 4-vinyl pyridine and 2-vinyl-5-ethyl pyridine, acrylonitrile, methacrylonitrile, methacrylic acid and acrylic acid. Mixtures of the monomeric age resistors and mixtures of the comonomers may be used. The monomer charge weight ratio is normally from about 0.10/99.9 to about 10/90 or even 20/80 monomeric age resistor/comonomer. The ratio may even be as high as 30/70, 40/60 or 50/50. A charge ratio of about 0.5/99.5 to about 5.0/95 is preferred.

Ratios will vary depending on the amount of age resistor desired to be bound and on the reactivity ratios of the monomers in the particular polymerization system used. However, the ratio may be even higher and the monomeric age resistor may even constitute all of the monomer charged, i.e., the ratio can be 100/0.

Preferably the monomer system contains at least 50 parts by weight per 100 parts by weight of total monomer of at least one diene, preferably a conjugated diene, such as 1,3-butadiene or isoprene.

One embodiment of the present invention involves the use of a monomer system comprised from about 50 to about 99.9 parts of at least one diene monomer, preferably a conjugated diene, 0 to about 49.9 parts of at least one monomer selected from the group consisting of vinyl monomers and vinylidene monomers and from about 0.10 to about 5.0 parts by weight of at least one monomeric age resistor, all parts being parts by weight per 100 parts by weight of total monomer. Preferably at least 0.5 part of monomeric age resistor is used. When at least 0.5 part of the monomeric age resistor is used, the upper limit on the diene monomer range is 99.5 parts and the upper limit of the vinyl monomer and/or vinylidene monomer range is 49.5 parts. The upper limit of the monomeric age resistor range may be even higher than 5.0, i.e., 10, 20, 30 and even 50.

The polymers resulting from the free radical polymerizations of monomeric systems containing the monomeric age resistors of the present invention contain at least one segmeric unit having the following structure.

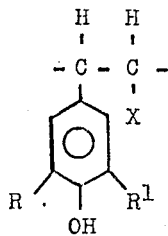

These polymers, whether liquid or solid, have a special advantage in that the age resistant portion is not extractable, and therefore the polymeric compositions are highly resistant to oxidative aging even after repeated exposure to aqueous detergent solutions or dry-cleaning fluids. This feature is especially significant where polymers are used in foam backings for rugs and where polymers are used in solution or latex form to treat fabrics, since such products are often exposed to aqueous detergent solutions or dry-cleaning fluids. This feature is also significant where factors such as contact with lubricating oils or exposure to high vacuum conditions are a consideration.

One of the advantages of the present process is that it permits the preparation of polymers prepared from monomer systems containing diene monomers and containing built-in stabilizers, without the formation of appreciable gel, that is, polymers can be made which are essentially gel-free. Gel formation is generally undesirable in a polymer since it can cause processing difficulties and directly and/or indirectly can affect the physical properties of the polymer in its vulcanized form. Normally a macro gel content of less than 50 percent is desirable. Preferably a gel content of less than 10 percent is desirable. Most preferably a gel content below 5 percent is desirable. Gel is the amount of polymer that is insoluble in an organic solvent such as benzene. One way to measure gel content comprises placing about 0.20 to about 0.30 grams of the polymer in 100 milliliters of benzene and permitting the mixture to stand for 48 hours. The mixture is then filtered through a 100 mesh stainless steel wire cloth having a wire diameter of 0.045 inch. A solids is then run on the filtrate to determine the amount of soluble polymer. The amount of gel is the difference between the amount of polymer placed in the benzene originally and the amount of soluble polymer. The percent gel is one hundred times the gel weight divided by the original polymer weight.

To afford adequate protection against degradation the polymers should contain from about 0.10 part to about 10.0 parts by weight of the segmeric form of the monomeric age resistor per 100 parts by weight of the polymer, although from about 0.50 part to about 5.0 parts is normally satisfactory, from about 0.50 part to about 3.0 parts being preferred. As much as 20 parts, 30 parts, 50 parts and more of the polymer may consist of the age resistor segmeric unit while the lower limit may be 0.50 part to 0.10 part and lower. In fact, polymers containing 100 percent age resistor segmeric units may be produced, if desired. However, as the amount of bound age resistor increases the physical characteristics of the polymer are altered accordingly. Where it is desired to produce a polymer which is self stabilizing and which substantially retains the physical properties of the comonomer or comonomers, normally the polymer should contain no more than about 10.0 parts by weight of the age resistor segmeric unit. Such polymers preferably are solid, although they may be liquid. Where it is desired that the polymer act as a polymeric age resistor which may be blended with unstabilized polymers the polymer should normally contain greater amounts of the monomeric age resistor, e.g., from about 10 up to 100 parts. The remainder of the polymer is comprised preferably of the segmeric form of at least one conjugated diene monomer and/or the segmeric form of at least one vinyl monomer. Preferably the polymers contain at least 50 percent by weight of the segmeric form of a diene, preferably a conjugated diene such as butadiene-1,3 or isoprene. Most preferred are polymers containing from about 50 to about 99.9 parts by weight of the segmeric form of at least one diene, preferably a conjugated diene, 0 to about 49.9 parts by weight of the segmeric form of at least one monomer selected from the group consisting of vinyl monomers and vinylidene monomers and 0.10 to 5.0 parts by weight of the segmeric form of at least one monomeric age resistor, all parts being by weight per 100 parts by weight of polymer. Preferably the polymer contains at least 0.5 part of the segmeric form of the monomeric age resistor. When the polymer contains at least 0.5 part of the segmeric form of the monomeric age resistor, the upper limit of diene segmer range is 99.5 parts and the upper limit of the vinyl segmer and/or vinylidene segmer range is 49.5 parts. The upper limit of the segmeric form of the monomeric age resistor range may be even higher than 5.0, i.e., 10, 20, 30 and even 50. In polymers generally prepared by free radical, particularly emulsion techniques, the trans 1,4 content is generally greater than the cis-1,4 or 1,2 content.

All of the phenolic compounds described herein, many of which are novel compounds, are capable of stabilizing polymers by simple incorporation into the polymers by conventional techniques such as by addition to polymer latices or by addition to the solid polymer on a mill or in a Banbury. When blending a self-stabilizing polymer with other polymers, especially when the self-stabilizing polymer contains large amounts of the segmeric form of the monomeric age resistor, one must consider the solubility problems involved in blending dissimilar polymers.

Polymers subject to deterioration by oxidation that can be conveniently protected by the age resistors described herein include substituted and unsubstituted, saturated and unsaturated, natural and synthetic polymers. The oxidizable natural polymers include natural rubber in its various forms, e.g., pale crepe and smoked sheet, and balata and gutta percha. The oxidizable synthetic polymers are prepared from a single monomer (homopolymer) or a mixture of two or more copolymerizable monomers (copolymers) wherein the monomers are combined in a random distribution or block form. The monomers may be substituted or unsubstituted and may possess one or more double bonds, or example, diene monomers, both conjugated and nonconjugated, and monoolefins including cyclic and acyclic monoolefins, especially vinyl and vinylidene monomers. Examples of conjugated dienes are 1,3-butadiene, isoprene, chloroprene, 2-ethyl-1,3-butadiene, 2,3-dimethyl-1,3-butadiene and piperylene. Examples of nonconjugated dienes are 1,4-pentadiene, 1,4-hexadiene, 1,5-hexadiene, dicyclopentadiene, 1,5-cyclooctadiene and ethylidene norbornene. Examples of acyclic monoolefins are ethylene, propylene, 1-butene, isobutylene, 1-pentene and 1-hexene. Examples of cyclic monoolefins are cyclopentene, cyclohexene, cycloheptene, cyclooctene and 4-methylcyclooctene. Examples of vinyl monomers are styrene, acrylonitrile, acrylic acid, ethylacrylate, butylacrylate, methyl vinyl ether, vinyl acetate and vinyl pyridine. Examples of vinylidene monomers are α-methylstyrene, methacrylic acid, methyl methacrylate, ethyl methacrylate, glycidyl methacrylate and vinylidene chloride. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene or acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene.

When added in free form normally 0.001 to 10.0 percent of the age resistor by weight, based on the weight of the polymer can be used, although the precise amount of the age resistors which is to be employed will depend somewhat on the nature of the polymer and the severity of the deteriorating conditions to which the polymer is to be exposed. In unsaturated polymers such as those made from conjugated dienes, the amount of age resistor necessary is greater than that required by a saturated polymer such as polyethylene. It has been found that an effective antioxidant amount of the disclosed stabilizers in rubbery unsaturated polymers will generally range from 0.05 to 5.0 percent by weight, i.e., parts by weight based on the weight of the polymer, although it is commonly preferred to use from 0.5 to 3.0 percent by weight, i.e., parts by weight based on the weight of the polymer. Mixtures of the age resistors may be used.

One of the advantages obtained in chemically combining the monomeric age resistors in the polymers by free radical polymerization techniques, as opposed to physically incorporating the antioxidant, e.g., by addition to the polymer latex or by milling or Banburying techniques, is that the age resistor is not extractable.

The following examples illustrate the practice of the present invention. Unless otherwise indicated, all parts are parts by weight.

Examples 1 to 6 illustrate the preparation of age resistors which can be used to stabilize polymers by physically combining the polymers therewith or which can be used in free radical polymerization systems as monomers to produce self-stabilizing polymers.

EXAMPLE 1

Ethyl 3,5-di tert.butyl-4-hydroxycinnamate was prepared by heating a mixture of 33.0 grams of 3,5-di tert.butyl-4-hydroxybenzaldehyde, 55.0 grams of ethyl hydrogen malonate, 50 milliliters of pyridine, and 3 milliliters of piperidine at 90° to 95° C. for 7 hours. The reaction mixture was cooled to room temperature and the solid which precipitated was filtered off, washed with 5 percent hydrochloric acid, and dried. Thirty grams of product was obtained which melted at 149° to 152° C. Working up the filtrate yielded an additional 5.5 grams of product.

EXAMPLE 2

3,5-di tert.butyl-4-hydroxycinnamonitrile was prepared by heating a mixture of 85.5 grams of 3,5-di tert.butyl-4-hydroxybenzaldehyde, 62 grams of cyanoacetic acid, 360 milliliters of pyridine, and 18 milliliters of piperidine at 80° C. for 3 hours. The reaction mixture was cooled to room temperature and poured into a mixture of 200 milliliters of concentrated hydrochloric acid and 350 grams of ice. The sticky solid tht precipitated was separated and recrystallized from petroleum ether. The yield was 48.8 grams of product which melted at 109° to 113° C.

EXAMPLE 3

3.5-di tert.butyl-4-hydroxycinnamamide was prepared by heating a mixture of 23.4 grams of 3,5-di tert.butyl-4-hydroxybenzaldehyde, 31 grams of malonic acid monoamide, 75 milliliters of pyridine, and 3 milliliters of piperidine at 90° to 100° C. for 10½ hours. The reaction mixture was poured into a solution of 75 milliliters of concentrated hydrochloric acid and 100 milliliters of water. The solid which precipitated was filtered off, dried, and recrystallized from benzene. Ten grams of product was obtained which melted at 217° to 219° C.

EXAMPLE 4

3,5-bis(1,1-dimethylbutyl)-4-hydroxybenzaldehyde was prepared by substituting 2,6-bis(1,1-dimethylbutyl)-p-cresol for 2,6-di tert.butyl-p-cresol in the procedure of Coffield, T. H., et al [J. Am. Chem. Soc. 79 5022(1957)] for preparing 2,6-di tert.butyl-4-hydroxybenzaldehyde.

One hundred thirty eight grams of 2,6-bis(1,1-dimethylbutyl)-p-cresol was dissolved in 700 milliliters of tert.butyl alcohol and 320 grams of bromine was added dropwise in 2 hours. The temperature rose from 22° to 57° C. during the addition. The reaction mixture was stirred for 1½ hours and was then cooled to 10° C. The solid which precipitated was filtered off, washed with a 10 percent solution of sodium thiosulfate, and dried. The yield of product was 29.2 grams and the melting point was 90° to 92° C.

The filtrate was concentrated and cooled. A further amount of product was obtained which after washing with 10 per cent sodium thiosulfate solution and then with hexane weighed 43.5 grams and also melted at 90° to 92° C.

Ethyl 3,5-bis(1,1-dimethylbutyl)-4-hydroxycinnamate was prepared by heating a mixture of 29 grams of 3,5-bis(1,1-dimethylbutyl)-4-hydroxybenzaldehyde, 40 grams of ethyl hydrogen malonate, 50 milliliters pyridine and 3 milliliters of piperidine at 90° to 95° C. for 7 hours. The reaction mixture was poured into a solution of 50 milliliters of concentrated hydrochloric acid in 100 milliliters of water. The oil which precipitated was separated by extraction with petroleum ether and the extract was stripped under vacuum to a pot temperature of 50°C./14 mm. The viscous residue weighed 39 grams.

EXAMPLE 5

3,5-bis(1,1-dimethylbutyl)-4-hydroxycinnamonitrile was prepared by heating a mixture of 29 grams of 3,5-bis(1,1-dimethylbutyl)-4-hydroxybenzaldehyde, 25.5 grams of cyanoacetic acid, 75 milliliters of pyridine, and 3 milliliters of piperidine at 95° to 100° C. for 7 hours. The reaction mixture was poured into a solution of 50 milliliters of concentrated hydrochloric acid in 100 milliliters of water. The oil which precipitated was separated by extraction with petroleum ether and the extract was stripped under vacuum to a pot temperature of 50° C./13 mm. The residue, which weighed 32 grams, was a viscous liquid which crystallized slowly on standing.

EXAMPLE 6

3,5-di tert.butyl-4-hydroxystyryl methyl ketone was prepared by adding a solution of 8 grams of sodium hydroxide in 100 milliliters of absolute ethanol to a mixture of 23.4 grams of 3,5-di tert.butyl-4-hydroxybenzaldehyde and 58 grams of acetone. The reaction mixture was stirred at room temperature for 14 hours and then at reflux temperature for 7½ hours. After cooling, it was poured into 500 milliliters of water and the resulting mixture was neutralized by the addition of dilute hydrochloric acid. The sticky solid which precipitated was filtered off and mixed with petroleum ether. Filtration yielded 11 grams of unreacted 3,5-di tert.butyl-4-hydroxybenzaldehyde. From the filtrate was isolated 5.5 grams of the desired product which melted at 101° to 105° C.

The following examples illustrate the preparation of polymers containing monomeric age resistors as part of the polymeric chain. They also illustrate the age resistance possessed by polymers having the monomeric age resistors physically combined therewith. Unless otherwise indicated all parts are parts by weight.

EXAMPLES 7 to 12

In Example 7 one gram of ethyl 3,5-di tert.butyl-4-hydroxycinnamate was added to 38 milliliters of an aqueous solution containing 0.8 gram of alkyl aryl sulfonate, 0.026 gram of the sodium salt of condensed naphthalene sulfonic acid and 0.08 gram of tripotassium phosphate. To this mixture was added 6 drops of tert.dodecylmercaptan, 5 grams of acrylonitrile and 15 grams of butadiene-1,3. To this combination was added 3.5 milliliters of an aqueous solution containing 0.008 gram of a 10/90 mixture of the monosodium salt of N,N-di(alpha-hydroxyethyl) glycine and the tetrasodium salt of ethylene diamine tetraacetic acid, 0.008 gram of $FeSO_4 \cdot 7 H_2O$ and 0.006 gram of sodium formaldehyde sulfoxylate. To this was was added 0.24 milliliter of a benzene solution containing 0.012 gram of p-menthane hydroperoxide. The polymerizations were run in a polymerization bath at 25° C. for 17 hours. The polymer was coagulated by adding the latex to 250 milliliters of isopropyl alcohol. It was then washed thoroughly with water and allowed to dry. In Examples 8 to 12 the same procedure as described for Example 7 was followed with the exception that other monomeric age resistors were substituted for the ethyl 3,5-di tert.butyl-4-hydroxycinnamate.

Table I contains oxygen absorption data for polymers of the present invention prepared by emulsion polymerization techniques from monomer systems containing monomeric age resistors of the present invention. The polymerizations were similar if not identical to those described in Examples 7 to 12. The monomer systems contained 75 parts of butadiene, 25 parts of acrylonitrile and 1.25 parts of the monomeric age resistor. Table I also contains oxygen absorption data on a polymer prepared from a polymerization recipe containing no monomeric age resistor. Table I also contains oxygen absorption data for SBR-1006 (butadiene/styrene elastomer) containing monomeric age resistors physically incorporated therein.

Before oxygen absorption tests were run on the polymers prepared from the monomeric age resistors, the dry polymers were extracted for 48 hours with methanol in a Soxhlet type apparatus to remove any of the free monomeric age resistor, dried again, and then dissolved in benzene. The benzene solutions were poured into aluminum trays and the solvent was allowed to evaporate. The resulting films were placed in an oxygen absorption apparatus. The amount of oxygen absorbed in a particular interval of time was determined and is listed in the following Table I. The testing procedure is described in further detail in *Industrial and Engineering Chemistry*, Vol. 43, page 456 (1951) and *Industrial and Engineering Chemistry*, Vol. 45, page 392 (1953).

The SBR polymer (1006) in Table I was dissolved in benzene and benzene solutions of the age resistors were added to portions of the SBR solutions to provide 1.00 part of he age resistors per 100 parts of rubbery polymer. The benzene solutions were used to form films and tested in oxygen absorption apparatus as described above.

Table I

| Monomeric Antioxidant | Hours to 1% Oxygen Absorbed | |
|---|---|---|
| | Built-In (90°C) | SBR-1006 (100°C) |
| None | 1 | — |
| Ethyl 3,5-di tert.butyl-4-hydroxycinnamate | 325 | 603 |
| 3,5-di tert.butyl-4-hydroxycinnamonitrile | 242 | 525 |
| 3,5-di tert.butyl-4-hydroxycinnamamide | 234 | 96 not completely soluble |
| Ethyl 3,5-bis(1,1-dimethylbutyl)-4-hydroxycinnamate | 56 | 379 |
| 3,5-bis(1,1-dimethylbutyl)-4-hydroxycinnamonitrile | 60 | 432 |
| 3,5-di tert.butyl-4-hydroxystyryl methyl ketone | 175 | 477 |

In Examples 13 and 14, SBR type polymers were prepared.

In Example 13, a copolymer of butadiene, styrene and 3,5-di tert.butyl-4-hydroxycinnamonitrile was made by polymerizing in 4-ounce bottles using the following proportions of ingredients.

| | Parts |
|---|---|
| butadiene-1,3 | 75.0 |
| styrene | 25.0 |
| 3,5-di tert.butyl-4-hydroxycinnamonitrile[1] | 1.25 |
| methylethylketone | 11.25 |
| tertiary dodecyl mercaptan | 0.50 |
| potassium soap of disproportionated rosin acids | 2.25 |
| sodium soap of tallow fatty acids | 2.25 |
| tripotassium phosphate | 0.25 |
| sodium salt of condensed naphthalene sulfonic acid | 0.08 |
| water | 200.0 |
| chelating agent[2] | 0.074 |
| FeSO$_4$.7 H$_2$O | 0.015 |
| sodium formaldehyde sulfoxylate | 0.05 |
| sodium hydrosulfite | 0.056 |
| paramenthane hydroperoxide | 0.12 |

[1]The antioxidant monomer was dissolved in methylethylketone before charging.
[2]The 10/90 glycine salt mixture of Examples 7 to 12.

Polymerization was accomplished at 5° C. A conversion of 76 per cent was reached after 18 hours. The polymer was coagulated in acidified 2-propanol and washed in methanol, then vacuum dried at 60° C.

In Example 14 butadiene, styrene and ethyl-3,5-di tert. butyl-4-hydroxycinnamate was polymerized in 4-ounce bottles. 2.5 parts of antioxidant monomer per 100 parts of the other monomers were charged. The recipe was similar to that of Example 13 except that no solvent (methylethylketone) was used to dissolve the monomeric age resistor. A conversion of 80 percent was reached after a reaction time of at least 16 hours. The polymer was coagulated and washed in 2-propanol, rinsed with methanol and dried at 160° F. in a forced draft oven.

Table II contains oxygen absorption data for polymers of the present invention prepared by emulsion polymerization techniques from monomer systems containing monomeric age resistors of the present invention. The polymerizations were similar if not identical to those described in Examples 13 and 14. The monomer systems contained 75 parts of butadiene, 25 parts of styrene and 1.25 parts of the monomeric age resistor.

Table II

| Antioxidant | Hours to 1% Oxygen Absorbed Built-In (100°C.) |
|---|---|
| 3,5-di tert.butyl-4-hydroxycinnamonitrile | 329 |
| Ethyl 3,5-di tert.butyl-4-hydroxycinnamate | 225 |

The above data demonstrate that the monomeric age resistors described herein are capable of providing age resistant polymeric compositions by either polymerizing the monomeric age resistor in a free radical polymerization system along with comonomers or by incorporating the monomeric age resistors by conventional techniques into the polymers. That is, the age resistors provide protection whether in a free or bound condition. Any of the monomeric age resistors, comonomers or polymers described earlier herein can be substituted for their counterparts in the above working examples to provide age resistant polymeric compositions. Also, free radical polymerization systems other than emulsion and solution systems, for example, free radical suspension systems, may also be used If desired, the monomer system can consist entirely of the age resistant monomer or monomers. Other initiator systems as described earlier herein can be substituted for the systems used in Examples 7 to 14. Naturally certain changes in variables such as the emulsification system to be used may be necessary as a result of the use of different monomers. However, such changes would be routine to those skilled in the art.

For example, in Examples 7 to 14, isoprene could have been substituted for the butadiene. Likewise vinylidene chloride or 2-vinyl pyridine could have been substituted for the styrene or acrylonitrile used in said examples. 3-tert.amyl-5-(1,1-dimethylbutyl)-4-hydroxycinnamamide or methyl 3-tert.butyl-5-(1,1-dimethylpentyl)-4-hydroxycinnamate could have been substituted for any of the monomeric age resistors described in any of said examples. Also for example, tert.butyl hydroperoxide could have been substituted for paramethane hydroperoxide in Example 7 at a level of, for example 0.03 to 0.04 part.

All of the polymers described in Examples 7 to 14 were solid elastomers.

Naturally polymerization rates and amounts of bound monomer can vary, as well as the type of emulsifier to be used depending upon the monomers used. Also, reactor size and degree of agitation can affect polymerization rates. However, optimum conditions and systems can be determined based upon the above revelations by routine experimentation by one possessing ordinary skill in the art.

Polymerization rates can often be improved by using a purified monomeric age resistor and/or by raising the polymerization temperature, using more potent initiator systems, increasing the initiator level or by any of the conventional means of improving polymerization rates.

All polymer molecular weights referred to herein, unless otherwise indicated, are number average molecular weights.

The age resistant polymeric compositions prepared by chemically binding the age resistors or by physically incorporating them into polymers, are age resistant, whether in vulcanized or unvulcanized form. They may be used, depending on the particular polymer involved, in products such as tires, industrial rubber products, such as transmission belts and hose, and molded goods. Where the polymeric composition contains the age resistor as an integral part of the polymer chain, it is especially useful in applications where a product is frequently exposed to aqueous detergent solutions or dry-cleaning fluids, for example, in foam backings for rugs and in polymer treated fabrics.

While certain representative embodiments and details have been shown or the purpose of illustrating the invention, it will be apparent to those skilled in this art that various changes and modifications may be made therein without departing from the spirit or scope of the invention.

What is claimed is:

1. An age resistant polymeric composition comprising a polymer susceptible to oxygen degradation having incorporated therin a stabilizing amount of at least one phenolic compound having the following structural formula:

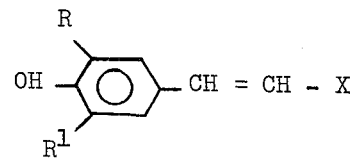

wherein R and $R^1$ are tertiary alkyl groups having 4 to 8 carbon atoms and wherein X is

wherein $R^3$ is selected from the group consisting of hydrogen and alkyl groups having from 1 to 4 carbon atoms.

2. The age resistant polymeric composition according to claim 1 wherein $R^3$ is selected from the group consisting of methyl and ethyl radicals.

3. The age resistant polymeric composition according to claim 2 wherein R and $R^1$ are tertiary butyl radicals.

4. The age resistant polymeric composition according to claim 1 wherein $R^3$ is ethyl.

5. The age resistant polymeric composition according to claim 1 wherein the polymer is selected from the group consisting of natural rubber and synthetic polymers prepared from conjugated diene monomers.

* * * * *

UNITED STATES PATENT AND TRADEMARK OFFICE
CERTIFICATE OF CORRECTION

PATENT NO. : 3,953,398
DATED : April 27, 1976
INVENTOR(S) : Richard H. Kline

It is certified that error appears in the above-identified patent and that said Letters Patent are hereby corrected as shown below:

Column 4, line 3 - "3 tert.butyl-5-(1,1,3,3-tert.butyl-4-hydroxybenzaldehyde" should be "3 tert.butyl-5-(1,1,3,3-tetramethylbutyl)-4-hydroxybenzaldehyde".

Column 5, lines 34 and 35 - "*number average molecular weights" should be placed at the bottom of the page as it is a footnote.

Column 5. Line 36 should read --attached. G. Manerke et al /Makromolekulare Chemie 99 175-185 (1966)/ pre- --.

Signed and Sealed this

Twenty-eighth Day of August 1979

[SEAL]

Attest:

LUTRELLE F. PARKER

Attesting Officer    Acting Commissioner of Patents and Trademarks